US007016473B1

(12) United States Patent
Linev et al.

(10) Patent No.: US 7,016,473 B1
(45) Date of Patent: Mar. 21, 2006

(54) METHOD OF BODY X-RAY SCANNING, AN APPARATUS FOR ITS IMPLEMENTATION AND A RADIATION DETECTOR (3 VERSION) THEREOF

(75) Inventors: Vladimir N. Linev, Minsk (BY); Anatoly I. Semenikov, Minsk (BY)

(73) Assignee: Naychno-Proizvodstvennoe Chastnoe Unitarnoe Predpriyatie "ADANI", Minsk (BY)

( * ) Notice: Subject to any disclaimer, the term of this patent is extended or adjusted under 35 U.S.C. 154(b) by 3 days.

(21) Appl. No.: 10/363,068

(22) PCT Filed: Aug. 28, 2000

(86) PCT No.: PCT/BY00/00005

§ 371 (c)(1),
(2), (4) Date: Feb. 28, 2003

(87) PCT Pub. No.: WO02/27306

PCT Pub. Date: Apr. 4, 2002

(51) Int. Cl.
*G21K 1/02* (2006.01)
(52) U.S. Cl. .......................... 378/146; 378/57
(58) Field of Classification Search .............. 378/148, 378/57, 55, 68–69, 24–26, 53, 54, 62, 208, 378/38–39, 146, 147
See application file for complete search history.

(56) References Cited

U.S. PATENT DOCUMENTS

| 3,050,626 | A | * | 8/1962 | Dukes et al. ............... 378/51 |
| 4,599,740 | A | * | 7/1986 | Cable ............................ 378/57 |
| 4,709,382 | A | * | 11/1987 | Sones .......................... 378/62 |
| 5,040,188 | A | | 8/1991 | Lang et al. |

(Continued)

OTHER PUBLICATIONS

Europ Scan "Controlix Vision", 3 pages from catalog.

(Continued)

*Primary Examiner*—David V. Bruce
*Assistant Examiner*—Hoon Song
(74) *Attorney, Agent, or Firm*—Jordan and Hamburg LLP

(57) ABSTRACT

The invention relates to the field of engineering physics in particular to the technique for detecting X-radiation, and it may be used for photometry, dosimetry as well as for measuring of space energy characteristics of optical-and-ionizing radiation fields with the aim of body X-ray scanning, human body in particular, to identify thereon or therein some highly undesirable objects or substances both for medical and security applications i.e. to prevent thefts and acts of terrorism and to provide the security of residential and other buildings that is in airports, banks and other high-risk areas. The X-ray screening of the body is realized by means of scanning it with a pre-shaped collimated bunch of X-radiation of low intensity due to moving the body and a source of X-radiation provided relative to one another, reception of X-radiation transmitted by the body, shaping and analysis of the image in its electronic form. It is the aim of the present invention to design a method and an apparatus which alongside with being safe and efficient make it possible to provide full body scanning with high precision. The aim set forth has been achieved by shaping the bunch of X-radiation as a single flat beam while X-radiation received at each scanning instant and converted into visible light radiation is in its turn converted into digital electronic signals. The radiation detectors filed are featuring a decreased noise level alongside with increased sensitivity and precision for registration of the intensity of X-radiation and also an extended dynamic range of X-radiation intensity values being registered which makes it possible to provide implementation of the method and the apparatus filed in the most advantageous way.

24 Claims, 7 Drawing Sheets

U.S. PATENT DOCUMENTS

| | | |
|---|---|---|
| 5,040,199 A | 8/1991 | Stein |
| 5,237,599 A * | 8/1993 | Gunji et al. ............... 378/148 |
| 5,404,387 A | 4/1995 | Hammond et al. |
| 5,511,106 A * | 4/1996 | Doebert et al. ............ 378/146 |
| 5,835,562 A * | 11/1998 | Ramsdell et al. ........... 378/206 |
| 5,838,758 A * | 11/1998 | Krug et al. .................. 378/53 |
| 5,850,836 A | 12/1998 | Steiger et al. |
| 6,094,472 A * | 7/2000 | Smith ......................... 378/86 |
| 6,347,132 B1 * | 2/2002 | Annis .......................... 378/57 |
| 6,504,898 B1 * | 1/2003 | Kotler et al. ................. 378/64 |

OTHER PUBLICATIONS

American Science & Engineering, Inc. BodySearch MICRO-DOSE personnel inspection system, 3 catalog pages.

* cited by examiner

METHOD OF BODY X-RAY SCANNING, AN APPARATUS FOR ITS IMPLEMENTATION AND A RADIATION DETECTOR (3 VERSION) THEREOF

FIELD OF THE INVENTION

The invention relates to the field of engineering physics, in particular to the technique for detecting X-radiation and it may be used for photometry, dosimetry as well as for measuring of space energy characteristics of optical-and-ionizing radiation fields with the aim of body X-ray scanning, human body in particular, to identify thereon or therein some highly undesirable objects or substances both for medical and security applications i.e. to prevent thefts and acts of terrorism and to provide the security of residential and other buildings that is in airports, banks and other high-risk areas.

PRIOR ART

Nowadays problems of body X-ray scanning and of human bodies, in particular, to identify thereon or therein some highly undesirable objects or substances acquire special importance. This can be related for instance to the necessity of early diagnosis of various hard diseases such as tumours or tuberculosis. Security applications among many others may include theft prevention of drugs or precious stones and metals as well as provision of the security of air flights and that of banks, embassies, nuclear power centers and other high-risk areas. X-ray luggage examination (introspection) in airports is nowadays the most efficient way to provide the security of air flights. X-ray luggage examination systems (See the brochure of EUROPE SCAN COMPANY) are designed as a conveyer passing through a rectangular frame with an X-ray source being installed in the upper part of said frame and a receptor of X-radiation being installed in the lower part of the frame under the conveyer. The apparatus just described is not designed for scanning of the passengers due to high level irradiation of an X-ray source which is used to increase the resolution of the apparatus.

Scanning of passengers for the presence of metallic objects hidden under clothing is provided with the help of electromagnetic frames and metal detectors. An X-ray method hasn't been used for the examination due to its danger for health safety.

A number of efforts have been attempted lately to use low-dose X-ray scanning which could be applied for the examination of people without any threat for their health.

Known is a method and an apparatus for X-ray scanning (product name Body Search, see the brochure of American Science and Engineering). A person is scanned with a beam of X-radiation of sufficiently low intensity, while the radiation transmitted by the person's body is converted into an image which is used to judge on the presence of concealed objects. An apparatus for implementation of the method is comprised of a cabinet with an X-ray source of low intensity positioned therein, means for shaping an X-ray beam and a detector of X-radiation transmitted. Close to the cabinet there is located a movable carrier which is open on three sides. A person to be scanned is standing upright on the platform close to the cabinet with his/her face or back towards the latter. An X-ray source positioned at approximately half the person's height radiates a fanned divergent X-ray beam of low intensity which, when transmitted through the clothing, is reflected from the surface of the person's body. The X-radiation thus reflected is trapped by the detector to create thereon an image of the contents being available on the surface of the body, in the clothing or on the clothing of the portion of the body turned towards the cabinet. For full examination it is necessary to make scanning in two positions i.e. the face towards the cabinet and the back towards the latter. With this method the internal cavities of the body which at present are very often used for concealment of drugs and precious stones are not subjected to the examination.

Besides, the strongest radiation effects most sensitive of the human's organs which are located in the medium portion of the human's body, while the person's feet and especially shoes which also may be used for concealing the contraband appear to be out of view of the examiner.

Also known is a method and an apparatus for X-ray scanning of the body (U.S. Pat. No. 5,404,377, patented Apr. 4, 1995) by means of scanning the latter with a pre-shaped flat bunch of flat beams of X-radiation of low intensity by means of moving the body and an X-ray source relative to each other, reception of the X-radiation transmitted through the body, generating an optical image from this X-radiation, further transmitting and intensifying the optical image, generating an electronic image, and analysis of the latter.

In the apparatus described an X-ray source, a collimator of special design and a receptor made in the form of an array of the detectors of X-radiation are secured on a holder which moves relative to a stationary body. Each of the detectors of X-radiation contains the devices for generating an optical image from the X-radiation transmitted through the body, fibre-optic coupling elements, optic image magnifiers and means for converting an optical image to an electronic image. Visualization means include therein said receptor and means for processing said electronic image.

Since the transmission of information in the form of an optical image is usually accompanied by significant losses, the intermediate intensification of the image is required. To generate an image suitable for the conversion into an optical image a bunch (pile) of X-radiation beams is required, said beams having a definite height. A massive carrier with the devices supported thereon does not provide a sufficiently fast movement. Provision of a low dose received by the body on condition of a relatively low speed of movement of an X-ray source alongside with providing the intensity of X-radiation transmitted by the body sufficient to generate an optical image presents in itself rather a complicated problem.

Known is a radiation detector used for registration and photometry of optical radiation (Whitson G. 500 IC Implementation Circuits: Translated from English-M.: Mir, 1992, p. 278, p. 88).

A detector contains a photodiode connected in the plainest case either parallel to the load alpha in the series with the bias voltage source and with the load, while an ordinary input circuit of a current-or-charge amplifier is used as the load.

Known is a method and an apparatus for X-ray examination (U.S. Pat. No. 5,040,188, published Apr. 13, 1991) by means of X-raying said body with ah pre-shaped flat beam of X-radiation with the possibility of moving a source of X-radiation in relation to said body, reception of X-radiation transmitted through said body, generating an optical signal from said X-radiation, converting said optical signal into an electronic signal, providing analog-to-digital conversion, generating an electronic image and analysis of the latter.

A source of X-radiation, a special-design collimator and a receptor of X-radiation of the apparatus are rigidly secured on the holder. The holder may be moved in relation to the stationary body lying on a horizontal table and installed in the desired position. A receptor of X-radiation is made as an array of X-radiation detectors with each of said detectors containing a device for generating an optical image from X-radiation transmitted through the body and means for converting an optical image to an electronic one.

Visualization means include therein said receptor of X-radiation, an analog-to-digital converter and a device for processing said electronic image.

This technical solution does not provide for scanning the body on the whole but is designed for intense examination of its particular area.

Also known is a method and an apparatus for X-ray examination of the body (U.S. Pat. No. 5,850,836 published Dec. 22, 1998) by means of scanning it with a pre-shaped flat beam of X-radiation due to moving a source of X-radiation in relation to said body, reception of X-radiation transmitted through said body, conversion of said X-radiation into an electronic signal, providing analog-to-digital conversion, generating an electronic image and analysis of the latter.

A source of X-radiation, a special-design collimator and a receptor of X-radiation of the apparatus are rigidly secured on the holder which is moved in relation to the stationary body occupying a strictly specified position on a horizontal table. Visualization means include therein said receptor of X-radiation, an analog-to-digital converter and a device for processing said electronic image. According to one of the holder allocation embodiments a collimator and a receptor of X-radiation are positioned vertically and during scanning their movement along the body is provided due to the movement of the holder.

The speed of a massive holder with the devices fixed thereon cannot be sufficiently high. It is rather a complicated problem to preserve a minimum dose received by the body in combination with the power of X-radiation transmitted by the body, should a source of X-radiation move with a sufficiently low speed.

Known is a radiation detector used for registration and photometry of optical radiation (Whitson G. 500 IC Implementation Circuits: Translated from English-M.: Mir., 1992, p. 278, p. 88).

A detector contains a photodiode connected in the plainest case either parallel to the load or in the series with the bias voltage source and with the load, while an ordinary input circuit of a current-or-charge amplifier is used as the load.

Also known are one-dimensional or two-dimensional photodiode and phototransistor arrays (Zolotarev V. F. Non-vacuum Prototypes of CRTs:-M.: Energia, 1972, p. 216; Semiconductor Image Signal Formers: Edited by P. Jespers, F. Van de Ville and M. White; Translated from English-M.: Mir, 1979, p. 573) and also Image Receivers Employing Charge-Coupled Devices (CCD) (Charge-Coupled Devices: Translated from English/Edited by D. F. Barb.-M.: Mir, 1982, p. 240). These devices provide registration of optical energy characteristics in optical radiation fields.

Known are ionizing radiation detectors used for registration, dosimetry and spectrometry of nuclear radiation (Tsytovich A. P. Nuclear Electronics:-M.: Energoatomizdat, 1984, p.p. 5– 33). The circuit diagram of these detectors is analogous to that of the detectors of optical radiation where photodiodes are replaced by ionization chambers, proportional counters, semiconductor sensors, scintillation counters or photodiodes which are used in combination with scintillators (Tsytovich).

Known are coordinate-sensitive detectors of ionizing radiation (IRCD) for one-dimensional and two-dimensional analysis used in nuclear experimental technique to registrate traces of elementary particles and to measure space distribution of nuclear particle flow (Zanevsky U. V. Wire Detectors of Elementory Particles:-M.: Atomizdat. 1978; Klenner P. Silicon Detectors. Nuclear Technique Abroad, 1986, N 6, p.p. 35–40). These detectors present either an array of wire electrodes positioned in a common gas volume or an array of strip electrodes produced by the surface evaporation on silicon crystal, said strip electrodes being coupled to an electronic readout device of coordinate information.

Out of a number of known radiation detectors the detector described by (Whitson, G.) appears to be most closely related to the one filed if the technical subject-matter is considered. This detector comprises a photodiode connected either in parallel to the load or in series with the load and a bias voltage source while an input circuit of a DC-or-charge amplifier serves as the load. This detector is designed for the registration of optical radiation, and when a photodiode is combined with a scintillator it also can be used for the registration of ionizing radiation. The disadvantage of such a detector is its low sensitivity which is caused to a considerable extent by noise and zero drift of DC amplifier used as the load of said detector.

SUMMARY OF THE INVENTION

The main aim targeted by the invention filed is implementation of a precision low-dose X-ray scanning.

It is the aim of the present invention to design a method and an apparatus which alongside with being safe and efficient make it possible to provide full body scanning with high precision.

There is one more accompanying aim to be solved which concerns elimination of the influence of the environmental changes in one of the apparatus modifications.

It is another aim of the invention to design an apparatus for converting visible light radiation into an electronic signal featuring a decreased noise level alongside with increased sensitivity and precision for registration of the intensity of X-radiation and also an extended dynamic range of X-radiation intensity values being registered which makes it possible to provide implementation of the method and the apparatus filed in the most advantageous way.

The aim set forth in a method of X-ray screening the body by means of scanning it with a pre-shaped collimated bunch of X-radiation of low intensity due to moving the body and a source of X-radiation relative to one another, reception of X-radiation transmitted by the body, shaping and analysis of the image in its electronic form has been achieved by shaping the bunch of X-radiation as a single flat beam while X-radiation received at each scanning instant and converted into visible light radiation is in its turn converted into digital electronic signals.

Preferably a flat beam of X-radiation is shaped as a vertical one.

In one of the embodiments of the method a flat X-ray beam is moved in a horizontal plane relative to the stationary body, and a receptor of X-radiation is moved in a horizontal plane synchronously with said beam. Movement of a flat beam of X-radiation is provided by means of a horizontal movement of a collimator with the speed ratio of the receptor and the collimator being constant. Movement of the collimator is provided with the help of a drive mechanism with a step motor, while movement of the receptor of X-radiation is also provided by means of a drive mechanism with a step motor, and it is synchronized with the collimator movement by maintaining the pre-defined ratio of their rotational speeds.

In another embodiment of the method a body is moved relative to a stationary source of X-radiation and a receptor of X-radiation.

A flat beam of X-radiation in this case is shaped with the scattering angle in the vertical plane of 37–43° and positioned such that the horizontal plane transversing the bottom portion of the body cuts off the beam by 2–5°.

In an apparatus for X-ray screening of the body comprising a carrier for positioning the body, a signal processing device, a source of X-radiation of low intensity and a holder with a collimator and receptor positioned thereon, said receptor being comprised of the detectors of X-radiation, each containing first device for conversion of X-radiation transmitted by the body into visible light radiation and second device for conversion of visible light radiation into an electronic signal, the aim set forth is achieved by the receptor made in the form of a vertical array of radiation detectors, with each detector containing said second device provided with a digital output and closely adjoining said first device.

The collimator made in the form of at least one pair of parallel plates and the detector are positioned vertically.

Preferably the holder is positioned horizontally with the possibility of movement in the vertical plane parallel to itself in relation to a stationary carrier for supporting the body. The holder contains thereon the horizontal guides for movement there along of the receptor provided with the drive mechanism with the step motor. The holder also contains thereon the horizontal guides for movement there along of the collimator also provided with the drive mechanism with the step motor. Said drive mechanisms are connected to the control unit for keeping of the pre-defined ratio of the rotation speeds of said step motors. The source of X-radiation is secured with the possibility of rotation around the vertical axis, and it is connected by a telescopic bar to the collimator.

In an alternative embodiment of the apparatus the holder is made n-shaped and positioned vertically, while one of the holder racks contains a linear receptor secured thereon and the second rack contains a collimator.

The carrier for positioning the body is made with the possibility of movement between the racks of the holder transversely to its surface, and it is provided with a separate motor and the guides, while the carrier on the whole is provided with a safeguard.

The source of X-radiation is positioned on the outer side of said second rack 20–50% higher than the level of the carrier. The collimator is secured inside said second rack of the holder. The space between the source of X-radiation and the second rack is covered with an additional housing made in the form of a pyramid with the base of the pyramid closely adjoining said rack and the corner at the top equal to the largest scattering angle of the beam of X-rays, while the additional housing contains positioned vertically therein at least one additional collimator made in the form of at least one pair of parallel plates.

The receptor may be comprised of at least two parts with the upper one making up 60–70% of the total height of the receptor and positioned at the angle of 4–6° in relation to the vertical plane towards the carrier for positioning the body.

To eliminate the influence of environmental changes the upper bar between the vertical racks is made as the four rods passing through the respective corner holes of the four flat rectangular plates positioned pairwise approximately at one third of the rods length at each of their ends at equal distances from the rod end with the ends of the rods being used for securing to the vertical racks.

In the first embodiment of a radiation detector filed containing a sensitive element e.g. a photodiode and a load connected in series, the improvement of precision and sensitivity at measuring the intensity of radiation is provided by means of an extra use within the detector structure of a key transistor and an interrogation pulse generator with respective coupling of these components to the other detector components. As a result a photocurrent of the photodiode is converted from a constant current to a pulsed one, this making it possible to measure the lower values of the latter with higher precision owing to the fact that the amplifiers of current and charge are lacking low-frequency noise components such as flicker noise and zero drift which are so much characteristic of DC current amplifiers.

Connection parallel to the load of N groups of components, said groups being comprised of the transistor and the photodiode which are coupled to N outputs of the interrogation pulse generator, provides a new feature of the radiation detector i.e. the ability to analyze the space distribution of the intensity of radiation being registered. In comparison to the prior art one-dimensional photodiode arrays [3] the embodiment filed makes it possible to implement a more extended dynamic range of the intensity of the radiation being registered.

This results from the fact that the dynamic range determined as the ratio of the maximum intensity of the radiation being registered to the minimum one is pre-defined by the variation range of an electric charge which has been integrated by the photodiode capacitance as well as the variation range of the integration period of said charge. The variation range of the charge integrated by the photodiode capacitance is determined as the ratio of the maximum value of the charge which has been integrated to the noise charge of the amplifier used to register said charge. All the other conditions being equal, the variation range of the charge which has been integrated by the photodiode capacitance is directly proportional to the square root of said photodiode capacitance value since the maximum value of the charge which has been integrated by the photodiode increases in direct proportion to the value of its capacitance, while the value of the amplifier noise charge increases in direct proportion only to the square root of the capacitance value at its input [5]. The variation range of the photocurrent integration period, with said integration provided by the photodiode capacitance, is in its turn defined by the ratio of its maximum possible value to the minimum one. The maximum duration of the photocurrent integration period is defined by the leakage resistance of the photodiode and that of the transistor as well as by the isolation of the circuit board, and it increases in direct proportion to the increase of the total capacitance of the photodiode and the key transistor. The minimum duration of the photocurrent integration period is defined by the time constant of the total capacitance charge of the photodiode and that of the key transistor during the generation of an integrated charge read-out signal. The duration of this time constant is directly proportional to the total capacitance of the photodiode and that of the key transistor as well as to the resistance of the open key transistor. Thus, the dynamic range of the intensities of the radiation being registered appears to be the wider the larger the capacitance of the photodiode and the charge leakage resistance therefrom are as well as the lower the resistance of the open key transistor is. A peculiar feature of the design filed is that both field-effect transistors (as in known photodiode arrays) and bipolar transistors may be used as a key transistor of the detector. The possibility of using bipolar transistors as the key transistor of the detector filed, said bipolar transistors having a hundred times steeper slope of characteristic as compared to field-effect transistors, makes it possible to decrease the resistance, of the open key transistor by hundred times and respectively, at all the other conditions being equal to extend the dynamic range of the intensities of the radiation being registered by hundred times. To provide a pre-defined dynamic range of the intensities of the radiation being registered the capacitors with required capacitance are connected in parallel to the photodiodes. To decrease the amplifier noise the detector may comprise L loads.

In the second embodiment of the radiation detector filed containing a radiation sensitive element and a load the increase of sensitivity and precision at registration of the radiation intensity is also provided by means of an extra use within the detector structure of a transistor and an interrogation pulse generator with respective coupling of these components to the other detector components. Interconnection between a supply voltage busbar of N groups of components, said groups being comprised of a key transistor, a radiation sensitive element and a capacitor, all being connected to N outputs of the interrogation pulse generator, provides a new feature of the radiation detector i.e. the ability to analyze the space distribution of the intensity of the radiation being registered. In comparison to the prior art one-dimensional photodiode arrays the second embodiment of the detector filed (as well as the first one) makes it possible to implement a more extended dynamic range of the radiation intensities being registered, and it also provides the possibility of using the radiation sensitive elements demanding a high-tension power supply voltage for their operation, e.g. such as proportional counters, ionisation chambers, photoresistors etc., extending the area of the possible detector applications. The increase of sensitivity and precision during registration of the radiation as well as the extension of the dynamic range of the radiation being registered is achieved in the second embodiment of the invention filed by the technical solution employed in the first embodiment of the invention filed which has been conditioned by a number of reasons making it possible to achieve the same results. To decrease the amplifier noise the detector may contain L loads.

In the third embodiment of the radiation detector filed containing an radiation sensitive element and a load the increase of sensitivity and precision during registration of the intensity of radiation is also provided by means of an extra use within the detector structure of a key transistor and an interrogation pulse generator with respective coupling of these components to the other detector components. The increase of sensitivity and precision during registration of radiation is achieved in the invention filed by the technical solution employed in the first embodiment of the invention filed which has been conditioned by a number of reasons making it possible to achieve the same results. A capacitor of the appropriate capacitance is connected between the first electrode of the key transistor and a common bus to provide the required dynamic range of the intensities of the radiation being registered.

The examples of the invention implementation are illustrated by the drawings that follow wherein:

DETAILED DESCRIPTION OF THE INVENTION

Figure 1:
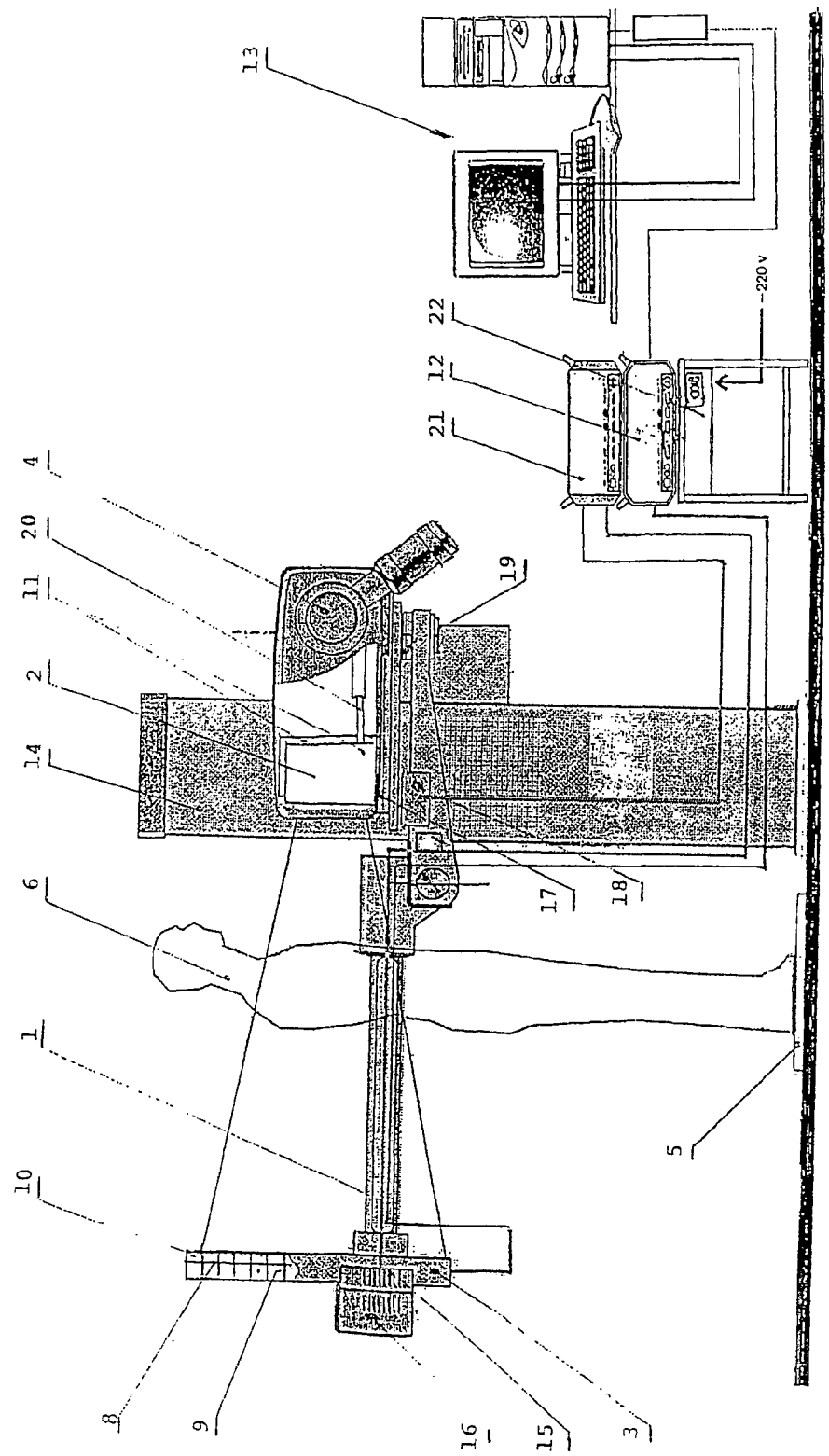
FIG. 1 is an overall view of the invention according to one of the preferred embodiments.
Figure 2:
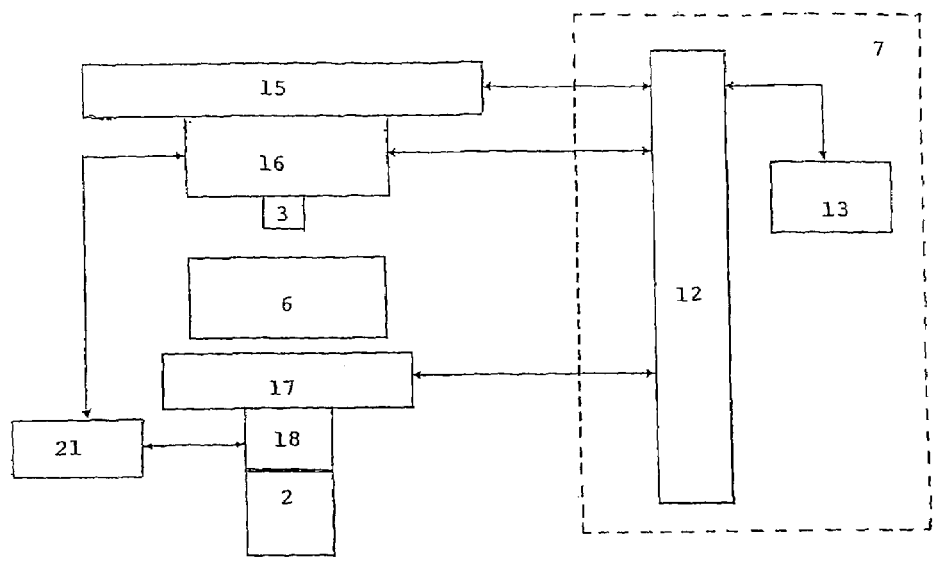
FIG. 2 illustrates an operational scheme of an apparatus in FIG. 1.
Figure 3:
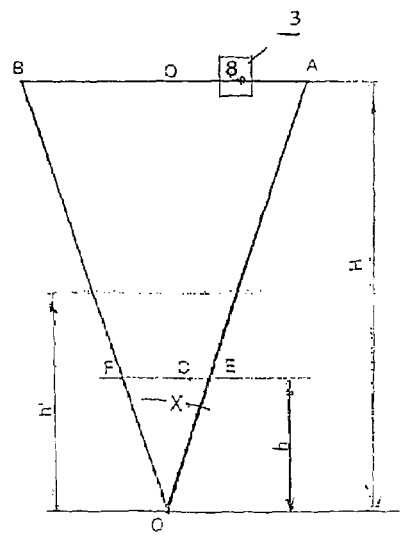
FIG. 3 shows the geometrical concept of a driving system.
Figure 4:
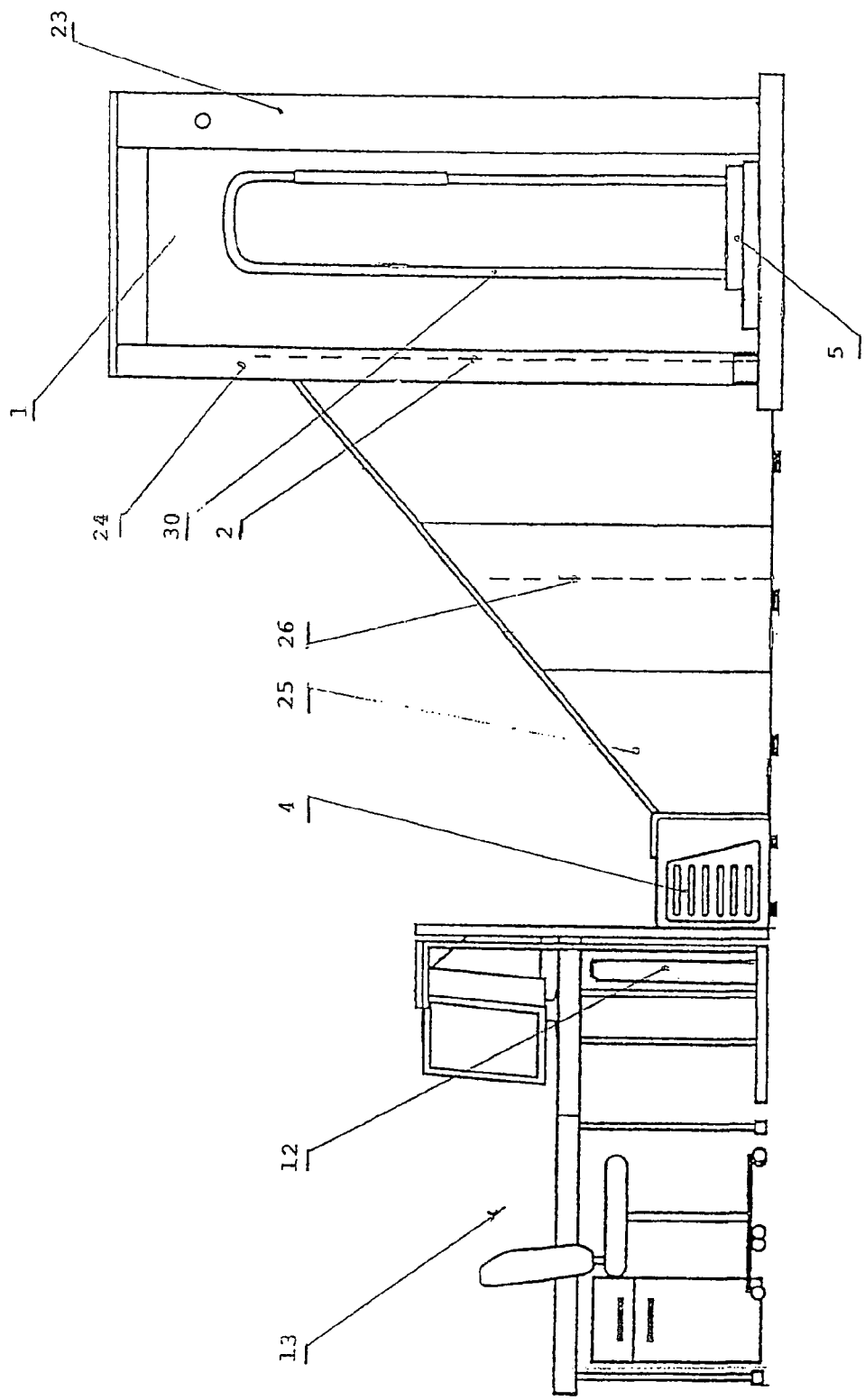
FIG. 4 is an overall view of the invention according to another preferred embodiment.

The present invention may find a great number of various applications, and it will be illustrated by way of the two of them as examples i.e. medical application illustrated by an apparatus in FIGS. 1–3 and nonmedical application illustrated by an apparatus in FIGS. 4–7.

A medical apparatus according to the invention shown in FIG. 1 comprises a holder 1 with a collimator 2 and a receptor 3 positioned thereon, a source 4 of X-radiation of low intensity, a carrier 5 for positioning a body 6, and a signal processing device 7 (see FIG. 2). The receptor 3 is made in the form of a vertical array of the detectors 8 of X-radiation, each containing a device 9 for converting visible light radiation into a digital electronic signal, said device closely adjoining a device 10 for converting X-radiation transmitted by the body into visible light radiation which may possibly be of scintillation type.

The collimator 2 made in the form of at least one pair of parallel plates and the receptor 3 are positioned vertically.

The signal processing device 7 (see FIG. 2) contains an interface unit 12 and a device 13 for processing the information thus received, said device possibly having the form of a computer—controlled operator's working station. An interface unit 12 is designed for control of all the apparatus units, check of their operations, conversion, and primary information processing. It is also used to provide the communication with the device 13 for information processing as well as to ensure the possibility of making the device 13 substantially distant from the source 4 of X-radiation with the aim of lowering the dosage of the service personnel.

In this apparatus a holder 1 is horizontally installed on a support 14 with the possibility of movement in the vertical plane parallel to itself in relation to a fixedly secured carrier 5 for positioning a body 6, possibly a patient. The holder 1 contains thereon horizontal guides 15 for movement there along of a receptor 3 by a drive mechanism provided with the step motor 16 and horizontal guides 17 for movement there along of a collimator 2 by a drive mechanism provided with the step motor 18. A source 4 of X-radiation as it is shown in FIG. 3 is installed on a hinge 19 with the possibility of rotating round the vertical axis, and it is coupled by a telescopic bar 20 with the collimator 2.

The above apparatus is provided with the control unit 21 for keeping of the pre-defined ratio of the rotation speeds of said step motors and the power supply unit 22 with connections (not shown) for applying the necessary voltages to the apparatus units.

A method filed has been implemented in the apparatus described in the following way.

The body 6 being scanned, possibly the human's body, referred to for the case described as "a patient" is positioned on the carrier 5. The holder 1 is being moved in the vertical plane to achieve the appropriate positioning of the collimator 2 and the receptor 3 in relation to portion of the patient's 6 body being screened dependent on the height of the latter. The collimator 2 and the receptor 3 are positioned with high precision such that this flat vertical beam of X-radiation always impinges the vertical array of the X-radiation detectors 8 which the receptor 3 is comprised of. After turning on of the step motors 16 and 18 the synchronous movement of the collimator 2 and that of the receptor 3 is started along the respective horizontal guides 15 and 16. The source 4 of X-radiation emits a bunch of beams which are shaped into one flat vertical beam by the collimator 2 with the help of two vertical plates 11. The movement of the collimator 2 and that of the receptor 3 is synchronized such that a flat beam always impinges the receptor 3.

FIG. 3 illustrates the synchronization concept of the driving system. During scanning the receptor 3 and respectively its detectors 8 of X-radiation are moving with the constant speed from point A to point B. The collimator 2 is being moved synchronously with the movement of said receptor but from point E to point F in such a way that the shadow projection of the slot of the collimator 2 of the flow of X-radiation emitted from point O always impinges the detectors 8.

The source 4 of X-radiation is positioned in point O. The direction of its maximum radiation which is synchronous with the scanning of the receptor 3 and the slot of the collimator 2 is changed in such a way that it is always to be located at the OC line.

Since the movement of the collimator 3 is always effected with the constant speed along the chord of the circumference with the center in point O, the rotational angular speed of the source 4 in point O will be changeable. The synchronous operation of the movement system is provided due to he fact that simultaneously with the movement of the collimator 2 the telescopic bar 20 of the source 4 which is rigidly connected to the collimator 2 is being rotated around the point O with the center of X-radiation being located therein too.

It evidently follows from the similarity concept that to achieve constant projection of the collimator 2 on the detectors 8 within the whole of the scanning range it is just sufficient to provide movement in time of both components according to one and the same law. This design concept makes it possible to provide implementation of the movement system with relatively comprehensive means since for synchronous movement it is just sufficient to provide movement of the collimator 2 and that of the receptor 3 with constant speeds.

The synchronous movement of the collimator 2 and that of the receptor 3 in this case may be achieved only if the ratio of their speeds is maintained with high precision. Since the rotational speed of the step motors is eventually defined by the commutation frequency of their windings the aim of the synchronous movement is confined to synthesizing of the two frequencies with the strictly defined ratio, while it is necessary to have the possibility of changing this ratio with very small increments. Besides, to increase the movement smoothness of the collimator 2 and that of the receptor 3 as well as to improve the synchronization of their operation the steps of the motors have been divided by 8 times, this causing the respective increase of the commutation frequency of the motors also by 8 times.

Taking into account that for example the angular rotational speeds of the collimator 2 and the receptor 3 make up respectively 10 and 2 rotations per second, the number of steps per rotation is equal to 200 and the division factor is equal to 8, the computational frequencies for controlling the motors will be respectively equal to 16000 Hz and 3200 Hz i.e. the step motors 16 and 18 make up respectively 12800 and 3200 of divided steps per second, while with scanning time of 4 sec. the collimator 2 and the receptor 3 make up respectively 6400 and 12800 of steps. It can be easily calculated that the step value of the receptor 3 with the number of steps being equal to 12800 and the duty cycle of 600 mm is equal to approximately 50 $\mu$m that is to provide the required synchronism of the duty cycle with the precision of 50 $\mu$m it is necessary to maintain the number of steps during the scanning period with the precision of one step and this in its turn means that the frequencies are to be maintained with the precision of not worse than 1/12800. The possibility also must be provided to change the frequencies for the required sampling of their ratio with the same increments (1/12800).

It appeared feasible to solve this problem with relatively comprehensive hardware means due to the fact that the two controlling frequencies greatly differ from one another (approximately in five times). This made it possible to design an electronic synchronization circuit in the following way. The unit 21 using an appropriate programmer provides synthesizing of the reference rotational frequency of the collimator motor 18 (higher frequency) which is equal to approximately 2000 Hz. The sampling precision of this frequency is not so much critical as it is related only to the scanning period, but not to the consistency of the movement. Each pulse of the reference frequency is sequentially interrogated in the memory array with the lower scanning frequency of the receptor 3 having been pre-recorded therein. The volume of this memory array makes up 65536 Byte i.e. it slightly exceeds the number of steps of the collimator 2. Consequently the position throughout the whole of the scanning area can be calculated and recorded in the memory with the precision of one step. The array to be stored is calculated on the grounds of the data received at the stage of system adjustment and alignment. The array stored is individual for each device. It is automatically loaded into the memory of the unit 21 without the operator's help just after the apparatus is turned on.

The duty cycle of the receptor 3 i.e. the distance between point A and B makes up 600 mm. The duty cycle of the collimator 2 i.e. the distance between points E and F makes up 150 mm. The distance H along the central axis OO' between the center of rotation O and the movement plane of the receptor 3 makes up 1600 mm. The distance h between the center of rotation and the movement plane of the collimator 2 makes up 400 mm. The distance h' between the center of rotation and the patient's location plane (designated by hatched line) depends on the dimension measurement of the patient and makes up within 800–900 mm i.e. it departs from the movement plane of the collimator 2 by 400–500 mm. The object geometrical increase factor (scaling factor) K which means the dimension ratio of the patient's shadow projection on the movement plane of the receptor 3 to the real dimensions of the patient will be equal to:

$$K=H/h'=2$$

The patient's scanning time T during which the receptor 3 moves from point A to point B may have the four fixed values: 2, 4, 8 and 16 sec. The basic operation mode corresponds to the scanning time of 4 sec. with the movement speed V of the receptor 3 during this time being equal to:

$$V=AB/T=600/4=150 \; mm/sec.$$

And the movement speed V of the collimator 2 being equal to $$V=EF/T=150/4=37.5 \; mm/sec.$$

In this operation mode (during scanning time of 4 sec.) the receptor 3 is being interrogated within t=10 msec.(0.01 sec.). Within this time the receptor 3 will move to the distances equal to $$S=V \times t=150 \times 0.01=1.5 \; mm$$

Evidently this value (1.5 mm) will correspond to the spatial resolution of the patient's image being detected in the receptor's plane along the horizontal axis. Taking into account the geometrical increase the spatial resolution S in the object's plane will make up $$S=S/K=1.5/2=0.75 \; mm$$

Consequently the movement values and the geometry of the system movement provide the spatial resolution of the object's image along the horizontal axis of 0.75 mm. The variation of the spatial resolution at variation of the scanning speed has directly proportional dependence i.e. when the speed is decreased, the spatial resolution is improved.

The receptor 3 may also be built as two vertical arrays of detectors 8 of X-radiation displaced by half the pitch in relation to positioning of detectors 8. These arrays may be interrogated either in sequential or in parallel mode during scanning. The positioning pitch of the detectors 8 makes up 1.55 mm. The vertical spatial resolution on the receptor surface for the case described will be twice as small as the positioning pitch of the detectors 8, thus making up approximately 0.8 mm. Taking into account a twofold geometric enlargement of the object (the object geometrical increase factor K=2) the vertical spatial resolution on the patient's location plane will be make up 0.4 mm.

A beam of X-radiation being transmitted by the patient's 6 body at each given scanning instant impinges the device 9 which may be for instance of scintillation type, and it is converted into visible light. This light being trapped by the devices 10 closely adjoining the devices 9 is further converted into digital electronic signals. The interrogation of the receptor 3 as it has been indicated is made within 10 msec. The output digital electronic signals are fed via the interface unit 12 to the device 13 for information processing. The dose received by the patient during one shot makes up from 0,3 to 0,9 mRem.

The movement of the collimator 2 and that of the receptor 3 both being light-weighted may be provided without practically any inertia with a wide range of speed adjustments.

Direct conversion of visible light signals into digital electronic signals eliminates the losses and makes it possible to provide an efficient examination by especially low doses of X-radiation.

In an alternative embodiment of an implementation example of an apparatus for nonmedical application illustrated in FIGS. 4–7 the components identical with those of the medical embodiment are shown by the same reference numerals.

In this embodiment a holder 1 is made n-shaped and positioned vertically with a linear receptor 3 secured to the first rack 23 of the holder 1 and a collimator 2 secured to the second rack 24. A carrier 5 for positioning the body has been made with the possibility of movement between the rack 23 and 24 of the holder 1 transversely to the holder plane, and it is provided with a separate motor and the guides (not shown).

Figure 5:
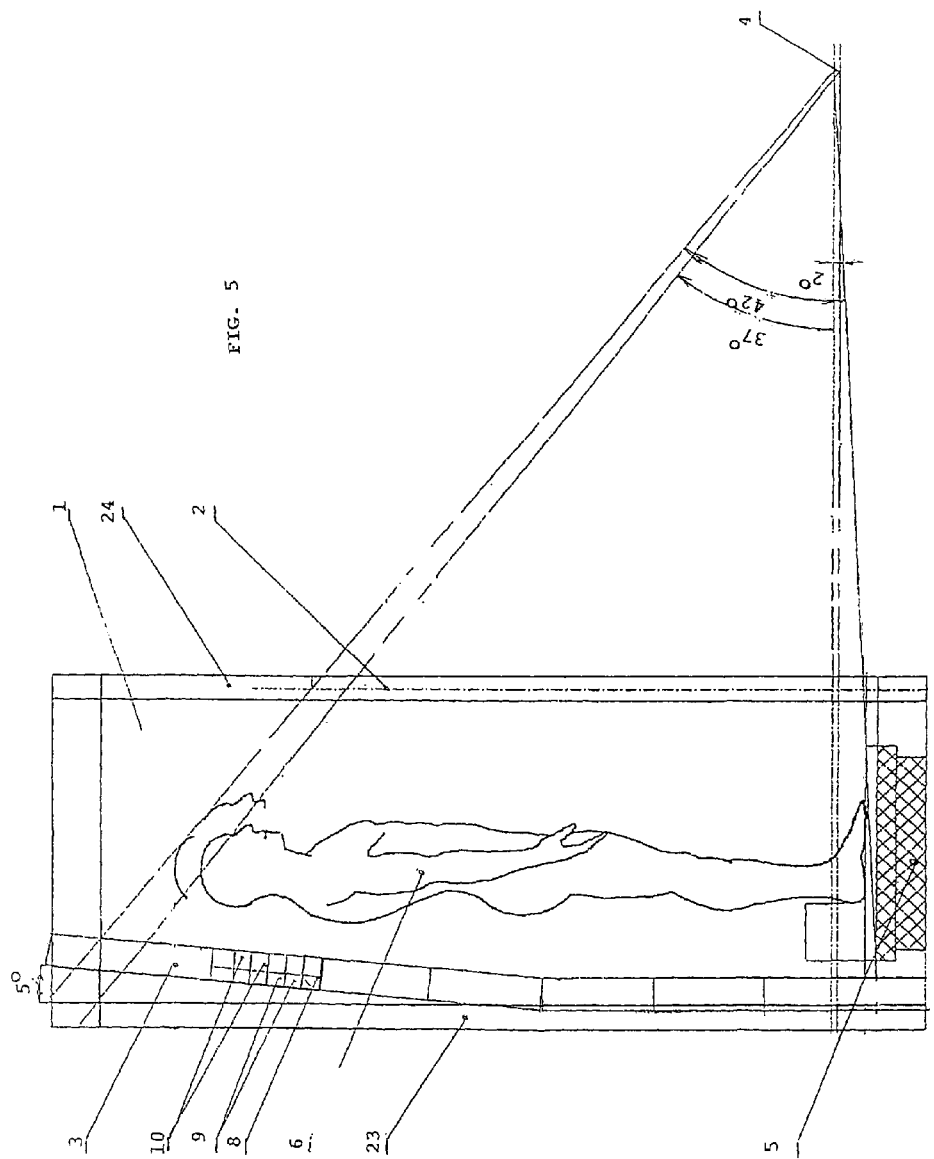
FIG. 5 illustrates an operational concept of an apparatus in FIG. 4 in the schematic form.

A source 4 of X-radiation is positioned on the outer side of said second rack 24 by 20–5.0% higher than the carrier 5 level (it is better shown at the FIG. 5). The collimator 2 is secured inside said second rack 24 of the holder. The space between the source 4 of X-radiation and the second rack 24 is covered with an additional housing 25 in the form of a pyramid with the base of said pyramid adjoining said rack 24 and the corner at the top being equal to the largest beam scattering angle. As it is shown in FIG. 5 this corner makes up about 43°.

Inside the additional housing 25 there is positioned vertically at least one additional collimator 26 made in the form of at least one pair of parallel plates.

The receptor 3 as it is shown in FIG. 5 may be comprised of two parts with the upper one making up 60–70% of the total height of the receptor and positioned at the angle of 4–6° in relation to the vertical plane towards the carrier 5.

Figure 6:
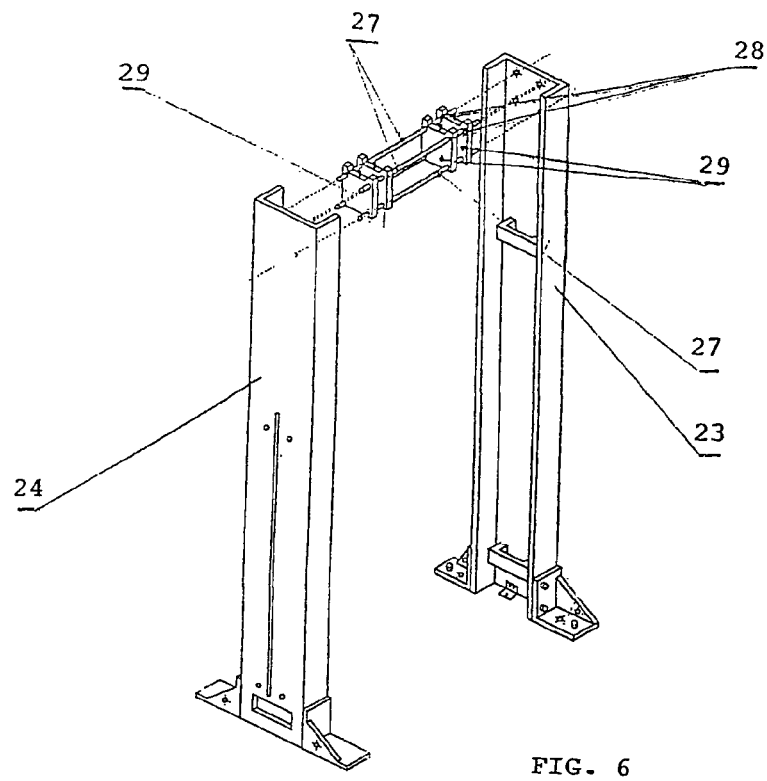
FIG. 6 shows the structure of a crossbar of an apparatus in FIG. 4.
Figure 7:
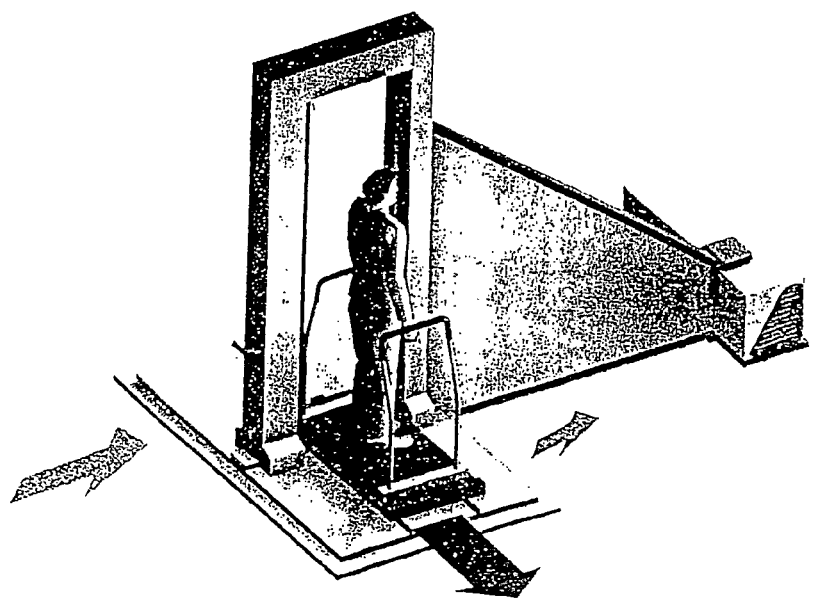
FIG. 7 illustrates movement through an apparatus in FIG. 4 in the schematic form.

The structure of the upper bar between the racks 23 and 24 is presented in FIG. 6. It is comprised of the four rods 27 passing through the respective corner holes 28 of the four flat rectangular plates 29. The plates 29 are positioned pairwise at approximately one third of the length of the rods 27 from each of their corners at equal distances from the rod end and pairwise in-between. The ends of the rods 27 are used for securing to the vertical racks 23 and 24 by the usual-type fixation means(not shown).

The carrier 5 for positioning the body 6 is provided with a safeguard 30.

The apparatus also contains the signal processing device 7 which contains an interface unit 12 and a device 13 for processing the information thus received, said device possibly having the form of a computer—controlled operator's working station. There is the power supply unit (not shown) for applying the necessary voltages to the apparatus units.

A method filed has been implemented in the apparatus described in the following way.

A flat vertical beam of X-radiation is generated from X-radiation emitted by the source 4 first with the help of at least one additional collimator 26 which is positioned vertically inside the additional housing 25. This housing protects the beam from its accidental crossing by any object or body. Then the flat vertical shape of the beam receives an extra shaping with the help of the basic collimator 2 secured in the rack 23 of the holder 1. The resulting beam of X-radiation is shaped with a scattering angle in the vertical plane of 37–43°. The collimator 2 and the receptor 3 are respectively positioned in the racks 23 ard 24 such that the flat beam always impinges a vertical array of the detectors 8 of X-radiation which the receptor 3 is comprised of The body 6 being scanned, possibly the human's body, referred to for the case described as "a passenger" is positioned onto the carrier 5 from it's first side. A safeguard 30 provides a support for the passenger when the carrier 5 is being moved and prevents his/her possible accidental falling from the moving carrier 5. A separate motor which may be an electric motor (not shown) provides movement of the carrier between the rack 23 and 24 in such a way that the passenger 6 traverses said flat vertical beam of X-radiation in such a way that horizontal plane transversing the bottom portion of the body i.e. the upper surface of the carrier 5 cuts off the beam by 2–5°. A beam of X-radiation transmitted by the passenger's 6 body impinges at each given scanning instant the device 9 which may be of scintillation type, and it is converted into visible light. This light is trapped by the devices 10 closely adjoining the devices 9, and it is converted into digital electronic signals. Output digital electronic signals are fed via an interface unit 12 to the device 13 for information processing. The passenger 6 having passed through the apparatus steps down from the carrier 5 at it's second side which is opposed to the first side (see FIG. 7).

The effective dose when examining people with an apparatus for nonmedical application is the most critical characteristic parameter. The calculation of doses in examining the human's body by directing X-rays through it at present is provided exclusively in medical radiological examination of the patients. A number of computer programs have been designed in various countries of the world exactly for medical radiology. The effective dose for examination of humans with an apparatus for nonmedical application filed has been approximately evaluated by means of known apparatus and methods.

For determination of the incoming dose the phantom of Alderson-Rando was used as well as the kit "N OMEX" of PTW-Freiburg (Germany) Company, the latter being comprised of a flat ionization chamber type 77335 with the total volume of 112 cm³.

The energy range of the chamber calibration was within from 39 keV to 95 keV with the correction factor being decreased from 1.04 to 0.99.

For carrying measurements on an apparatus for nonmedical application the use was made of a complex filter 6 mm Al+0.5 mm Cu. The tube voltage was varied from 120 to 200 kV. The effective radiation energy was varied from approximately 70 to 120 keV. The correction factor for the energy dependence of the chamber sensitivity $K_q$ was considered as equal to 1.

The measurement results are given in Table 1.

TABLE 1

| Tube voltage, kV 1 | Tube current mA 2 | Air kerma μ Gy 3 |
|---|---|---|
| Chamber positioned at chest level of phantom | | |
| 120 | 1 | 0,375 |
|  |  | 0,351 |
|  |  | 0,354 |
|  |  | 0,357 |
| 120 | 2 | 0,612 |
|  |  | 0,612 |
|  |  | 0,624 |
| 120 | 3 | 1,002 |
|  |  | 0,999 |
|  |  | 1,029 |
| 120 | 4 | 1,338 |
|  |  | 1,350 |
|  |  | 1,359 |

TABLE 1-continued

| Tube voltage, kV 1 | Tube current mA 2 | Air kerma μ Gy 3 |
|---|---|---|
| 120 | 5 | 1,611 |
|  |  | 1,623 |
|  |  | 1,638 |
| 120 | 7 | 2,268 |
|  |  | 2,277 |
|  |  | 2,289 |
| 130 | 1 | 0,438 |
|  |  | 0,438 |
|  |  | 0,426 |
| 130 | 2 | 0,804 |
|  |  | 0,804 |
|  |  | 0,801 |
| 130 | 3 | 1,275 |
|  |  | 1,290 |
|  |  | 1,278 |
| 130 | 4 | 1,701 |
|  |  | 1,722 |
|  |  | 1,719 |
| 130 | 5 | 2,094 |
|  |  | 2,094 |
|  |  | 2,097 |
|  |  | 2,100 |
| 130 | 6 | 2,520 |
|  |  | 2,532 |
|  |  | 2,524 |
| 140 | 1 | 0,519 |
|  |  | 0,516 |
|  |  | 0,519 |
| 140 | 2 | 1,002 |
|  |  | 1,002 |
| 140 | 3 | 1,611 |
|  |  | 1,611 |
| 140 | 4 | 2,163 |
|  |  | 2,172 |
| 140 | 5 | 2,607 |
|  |  | 2,628 |
| 140 | 6 | 3,108 |
|  |  | 3,129 |
| 150 | 1 | 0,648 |
|  |  | 0,654 |
| 150 | 2 | 1,224 |
|  |  | 1,233 |
| 150 | 3 | 1,983 |
|  |  | 1,938 |
| 150 | 4 | 2,661 |
|  |  | 2,655 |
| 150 | 5 | 3,243 |
|  |  | 3,273 |
| 160 | 1 | 0,741 |
|  |  | 0,759 |
| 160 | 2 | 1,404 |
|  |  | 1,461 |
|  |  | 1,452 |
| 160 | 3 | 2,331 |
|  |  | 2,337 |
| 160 | 4 | 3,138 |
|  |  | 3,162 |
| 160 | 5 | 3,870 |
|  |  | 3,879 |
| 170 | 1 | 0,885 |
|  |  | 0,885 |
| 170 | 2 | 1,725 |
|  |  | 1,728 |
| 170 | 3 | 2,730 |
|  |  | 2,784 |
| 170 | 4 | 3,705 |
|  |  | 3,753 |
| 170 | 5 | 4,569 |
|  |  | 4,563 |
| 180 | 1 | 1,011 |
|  |  | 1,002 |
| 180 | 2 | 1,962 |
|  |  | 1,953 |
| 180 | 3 | 3,171 |
|  |  | 3,171 |

TABLE 1-continued

| Tube voltage, kV 1 | Tube current mA 2 | Air kerma µ Gy 3 |
|---|---|---|
| 180 | 4 | 4,266 |
|  |  | 4,275 |
| 180 | 5 | 5,259 |
|  |  | 5,262 |
| 190 | 1 | 1,206 |
|  |  | 1,212 |
| 190 | 2 | 2,310 |
|  |  | 2,301 |
| 190 | 3 | 3,657 |
|  |  | 3,672 |
| 190 | 4 | 4,956 |
|  |  | 4,998 |
| 200 | 1 | 1,392 |
|  |  | 1,398 |
| 200 | 2 | 2,652 |
|  |  | 2,643 |
| 200 | 3 | 4,209 |
|  |  | 4,212 |
| Background measurement | | |
| 0 | 0 | 0,033 |
|  |  | 0,030 |
| Measurement behind phantom Chamber at chest level | | |
| 190 | 4 | 0,450 |
|  |  | 0,462 |
| 150 | 3 | 0,183 |
|  |  | 0,189 |
| Chamber at stomach level | | |
| 150 | 3 | 2,247 |
|  |  | 2,250 |
| 190 | 2 | 2,610 |
|  |  | 2,652 |
| Chamber at head level | | |
| 150 | 3 | 1,443 |
|  |  | 1,428 |
| 190 | 2 | 1,566 |
|  |  | 1,752 |

The study of the data received reveals that the doses in the bottom part of the body appeared to be higher than at head level. This can be explained by the fact that the source of irradiation was positioned at the distance of about 40 cm relative to the floor, and the source-to-object distance in the bottom part of the body appears to be less than in the upper part.

The calculation of effective dose was carried out by means of program "ORGDOSA" which is analogous to program PDS-60.

Since the program was designed for determination of an affective dose during medical X-ray examination, the radiation conditions on an apparatus for nonmedical application filed appear to be beyond the range of specifications covered by the program.

Generally speaking the limitations of specifications in the program do not differ from those in the dose measuring instruments i.e. source-to-object distance of not more than 200 cm, maximum tube voltage value 150 kV, minimum incoming dose $10\mu$ Gy etc. Therefore for calculation of an effective dose the well-known laws of physics concerning the interaction of an X-ray radiation with the substance were to be taken into account, i.e.:

1. With one and the same filter the increase of tube voltage results in the decrease of the incoming dose;
2. The increase of the source-to-object distance under the constant specifications of the tube results in the decrease of the incoming dose;
3. The program does not provide an X-ray examination of the whole body, therefore to make calculations the radiation field was divided into separate components i.e. head, chest, stomach, pelvis and hips with the calculation of the effective dose for the whole of the body from each component and further summing up of the results thus received. No contribution from ankles and foot to the total dose was accounted as the phantom of Alderson-Rando does not possess these, and the measurements at this level were not made.
4. The calculation was carried out for minimum incoming dose recorded in the program which was of $10\mu$ Gy with further equating of an amount of the effective dose to the measured input dose at the level considered.

An example of calculating the effective dose under X-ray examination of the phantom of Anderson-Rando by means of an apparatus for nonmedical application filed.

Tube voltage-150 kV.
Tube current-3 mA.
Distance of source-to-object input surface-20 cm.
Radiation field dimensions-chosen for each level i.e. head, chest, stomach, pelvis and hips.
Deff=$0.11\mu$ Sv for head,
Deff=$1.04\mu$ Sv for chest,
Deff=$1.19\mu$ Sv for stomach,
Deff=$1.13\mu$ Sv for pelvis,
Deff=$0.76\mu$ Sv for hips,
Deff=$4.23\mu$ Sv total.

Thus, the effective dose for examination of humans with an apparatus for nonmedical application filed may be approximately evaluated as the one not exceeding $5\mu$ Sv for any conditions of X-ray examination within the range of tube voltages not exceeding 150 kV and tube currents not exceeding 3 mA. However, the results thus received should be considered as particularly preliminary ones.

Due to the X-ray beam scattering angle in the vertical plane of 37–43° and low positioning of the source 4 of X-radiation such that the upper surface of the carrier 5 cuts off the beam by 2–5' the carrier 5 during just a single movement makes it possible to provide full scanning of the passenger's body 6 on the whole from the head to the shoes with identification therein or thereon of certain foreign articles.

The tilt of the upper part of the receptor 3 by 4–6° towards the carrier 5 provides for the compensation of the extension of the path of X-radiation up to this part of the receptor 3 and thus makes it possible to eliminate the impairment of the image quality of the upper portion of the body.

As it is seen in FIGS. 4–7, the height of this modification of an apparatus must be made min. 2,5 m to provide the examination of passengers of any height. However a n-shaped structure of such dimensions appears to be greatly sensitive to vibrations and environmental changes such as temperature etc. At temperature changes the structure will warp, this causing displacement of a flat beam from the linear receptor 3. To eliminate this effect the upper bar of the holder has been made as described above (see FIG. 6). The rods 27 provide redistribution of the tensions thus created into the four flat rectangular plates 29, which in turn redistribute and damp said tensions therein.

Figure 8:
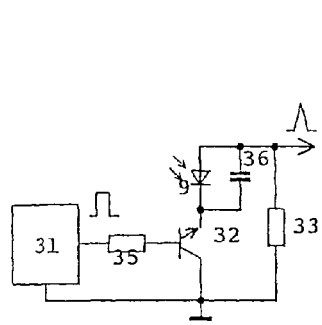
FIG. 8, 9, 10 illustrate the three modifications of a basic circuit of the first embodiment of the radiation detector filed which employs photodiodes as sensitive elements.
Figure 9:
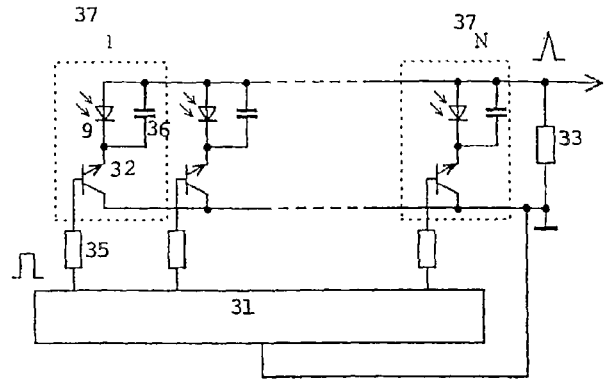
Figure 10:
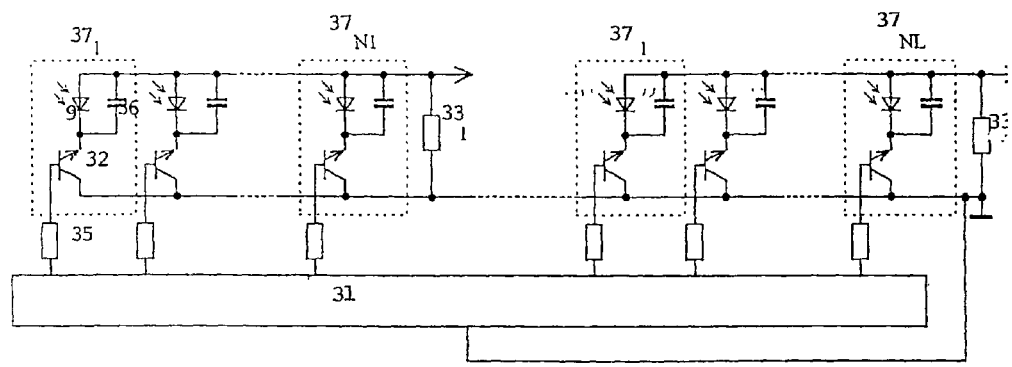

The detector 8 of X-radiation comprises an interrogation pulse generator 31, a radiation sensitive element 9 (for the first embodiment of the detector filed it is a photodiode), a key transistor 32, a load 33. In accordance with the second and the third embodiments the detector may also comprise a current-limiting resistor 34. In accordance with the first embodiment of the detector (see FIG. 8, 9, 10) the pliotodiode 9 and the load 33 are connected in series while the load 33 is connected by its signal output to the photodiode 9 and by the other end to a common bar. The second electrode of the photodiode 9 is connected to the first electrode (e.g. the emitter) of the key transistor 32, while the control electrode (e.g. the base) is connected via a resistor 35 to the output of the interrogation pulse generator 31 and the third electrode of the transistor 32 (e.g. the collector) is connected to the common bus. An integrating capacitor 36 may be connected in parallel to the photodiode 9. In the second modification of the first embodiment of the detector (see FIG. 9) the load 33 is connected in parallel to N groups of $37_1$, $37_2$, . . . $37_N$ components, each of said groups comprising seriesly connected the key transistor 32 and the photodiode 9 with the possibility of parallel connection to the latter of the integrating capacitor 34. Besides, the interrogation pulse generator 3 comprises N outputs, each of the latter being connected via the resistor 35 to the control electrode (the base) of the key transistor 32 from the respective group of components where N is an integer more than 1. In the third modification of the first embodiment of the detector (see FIG. 10) L loads $31_1$, $32_2$, . . . $31_L$ are used with Ni said groups of components being connected in parallel to an i-numbered load, and the interrogation pulse generator 31 contains M outputs where $M=\Sigma N_i$ and L, Ni are the integers more than 1.

Figure 11:
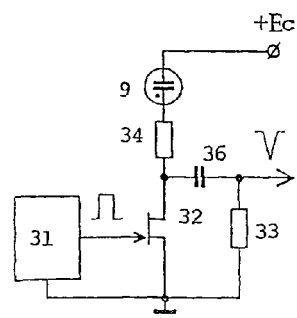
FIGS. 11, 12, 13 and 14 illustrate the four modifications of a basic circuit of the second embodiment of the radiation detector filed which employs various types of sensitive elements operating in the presence of a bias voltage including a high-tension voltage.
Figure 12:
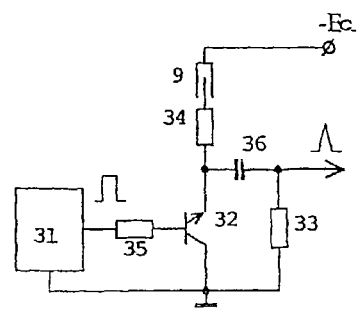

In the second embodiment of the detector filed (see FIG. 11, 12, 13, 14) it is possible to use as sensitive elements 9 besides photodiodes also other types of components such as ionization chambers for instance (see FIG. 11) or proportional counters of ionizing radiation (see FIG. 12, 13, 14). The detector filed (see FIG. 11, 12) in its first most ordinary modification of the second embodiment comprises the interrogation pulse generator 29, a radiation sensitive element 9, a key transistor 32, a load 33, a current-limiting resistor 32, and an intergrating capacitor 34.

In this combination a radiation sensitive element 9 is connected on the one end to a power supply bus and on the other end via the current-limiting resistor 34 to the first electrode (e.g. the drain or the emitter) of the key transistor 32 and to the first plate of the integrating capacitor 36 with the second plate of said capacitor being connected to the common bus. Besides, the output of the interrogation pulse generator 31 is connected to the control electrode (the gate or the base) of the key transistor 32. Should the key transistor 32 be a bipolar one, then there is connected a resistor 35 between the output of the generator 31 and the base of the transistor 32 (see FIG. 12). The third electrode (e.g. the source or the collector) of the key transistor 32 is connected to the common bus. The power supply bus is fed with constant voltage Ec of the appropriate polarity and value. Both field-effect transistors (see FIG. 11) and bipolar transistors (see FIG. 12) may be used as the key transistor 32.

Figure 13:
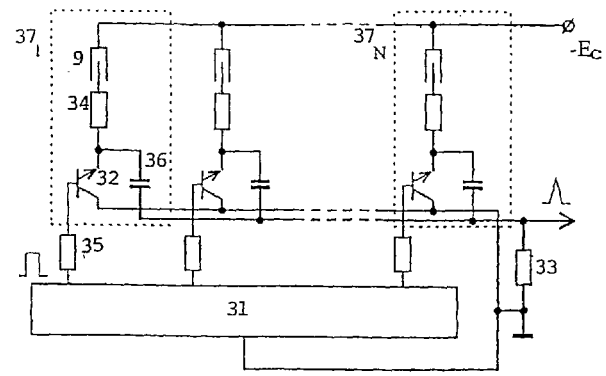
Figure 14:
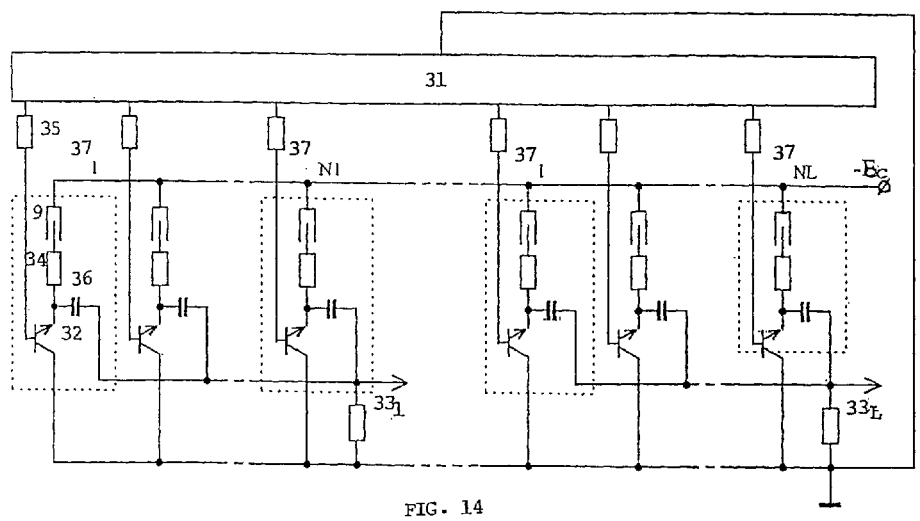

It is most feasible to use in the second embodiment of the detector filed the elements which are sensitive to various types of radiation, said elements demanding for their efficient operation the supply of a bias voltage including a high-tension one. In the second modification of the second embodiment of the radiation detector filed (see FIG. 13) between a power supply bus and a common bus there are connected N groups of $37_1$, $37_i$, . . . $37_N$ components, each of said groups being comprised of a seriesly connected radiation sensitive element 9 and a key transistor 32 with the common point of these being connected via an integrating capacitor 36 to the signal output of a load 33. Besides an interrogation pulse generator 31 contains N outputs with each of said outputs being connected via a resistor 35 to the control electrode (the base) of the key transistor 32 from the respective group of components where N is an integer more than 1. In the third modification of the second embodiment of the radiation detector (see FIG. 14) there is contained L loads $31_1$, $31_2$, . . . $31_L$, with the signal output of each i-numbered load being connected to Ni of above said groups of components, and an interrogation pulse generator contains M outputs where $M=\Sigma Ni$ and Li Ni are the integers more than 1.

Figure 15:
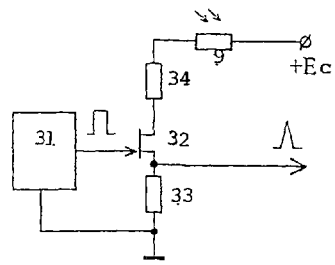
FIGS. 15 and 16 show the two modifications of a basic circuit of the third embodiment of the radiation detector filed using various types of sensitive elements operating in the presence of a bias voltage.
Figure 16:
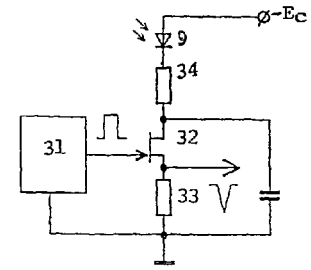

In the third embodiment of the radiation detector filed (see FIG. 15, 16) there is also provided the possibility of using besides the photodiodes of other types of sensitive elements 9 which demand for their efficient operation the supply of a bias voltage, for instance for the photoresistors (see FIG. 15). In the first most comprehensive modification of the third embodiment of the detector filed (see FIG. 15) there is contained a interrogation pulse generator 29, a radiation sensitive element 9, a key transistor 32, a load 33 and a current-limiting resistor 34. In this combination the radiation sensitive element is connected on the one end to a power supply bus and on the other end via the current-limiting resistor 34 to the first electrode (e.g. the drain) of the key transistor 32. The output of the interrogation pulse generator 31 is connected to the control electrode (e.g. the gate) of the key transistor 32, with the third electrode (e.g. the source) being connected to the signal output of the load 33 which is connected on the other side to the common bus. The power supply bus is fed with constant voltage Ec of the appropriate polarity and value. The second modification of the third embodiment of the radiation detector filed (see FIG. 16) additionally contains an integrating capacitor 34, which is connected between the first electrode (e.g. the drain) of the key transistor 32 and the common bus. The key transistor 32 in the third embodiment of the radiation detector filed must be exclusively of the field-effect type with the internal capacitance of this type of transistors being used as an integrating one in the first modification of this embodiment of the detector.

The interrogation pulse generator 31 in the radiation detector filed presents in itself a generator of rectangular tension pulses. The amplitude and the polarity of the voltage output pulses are chosen such that they could provide a turn-on mode of the respective key transistors of the detector. Multi-component modifications of the detector may employ as the generator 29 ring counters, deciphers, shift registers and other devices with the number of outputs of said devices being equal to the number of key transistors in the detector and the voltage pulses of the appropriate polarity amplitude and duration being generated at said outputs at respective time instants.

The operation of the radiation detector is provided in the following way. The current of the sensitive element 9 which is generated under the influence of the radiation is integrated by the common capacitance of the sensitive element 9 and parallel connected integrating capacitor 36 (see FIG. 8, 9, 10), by the capacitance of the integrating capacitor 36 (see FIGS. 11–14), by the internal capacitance of the key transistor 32 and the integrating capacitor 36 (see FIG. 16) during the period between the interrogations of the transistor 32. During the interrogation instant of the key transistor 32 an interrogation pulse is supplied from the output of the generator 31 to the control electrode of the transistor 32 with the polarity of said pulse providing the turn-on of the transistor 32. As a result of the turn-on of the transistor 32 the latter starts to conduct a current pulse which transfers a charge via the capacitor 36 and the load 33, said charge having been integrated by the capacitor 36 (and also by the capacitance of the sensitive element 9 or by the capacitance of the transistor 32). Concurrently with supplying the interrogation pulse the load 31 starts to pass the charges used to recharge the interelectrode capacitances of the transistor 32 via the capacitance of the sensitive element 9 and/or the integrating capacitor 36 (see FIGS. 8–14) or directly (see FIG. 15, 16). The charges of the same value but having the reverse polarity are coupled via said chains during takeoff of the interrogation pulse. As a result after supplying of each interrogation pulse the load 33 passes a total charge equal to the charge of the current of the sensitive element 9 which has been integrated by the capacitor 36 and/or proper capacitance of said sensitive element during the time between supplying of the interrogation pulses. Should the load 33 be connected between the key transistor 32 and the common bus (see FIGS. 15, 16), then after supplying of the interrogation pulse the current charge of the sensitive element 9 which has been integrated by the total capacitance of the capacitor 36 and/or the transistor 32 is transferred to the load 33. This charge is proportional to the flow of radiation which has been impinging the sensitive element 9 during the time between interrogations of the respective key transistor 32.

The interrogation pulse generator 31 used in multi-component modifications of the detector filed (see FIGS. 9, 10, 13, 14) is provided with a plurality of outputs with the tension pulses being generated at each of said outputs in a pre-defined sequence. During this operation there comes a sequential interrogation of the key transistors 30, which the group 37 of components is comprised of, this interrogation corresponding for instance to the coming in turn read-out of the respective integrating capacitor 36 with the current pulses being generated at the load, said pulses when added at respective time instants by the sync pulses could be presented as a videosignal, while the coordinate of the detector sensitive element is always defined by the number of corresponding to it pulse at the load or by the instant of the appearance of said pulse with the number of radiation particles which have been registered in this sensitive element being defined by the amplitude of the current pulse corresponding to said element. A series of readout current pulses in the modifications of the detector with several loads (see FIGS. 10, 14) is generated in turn at each of the loads during the interrogation time of the key transistors included in the groups 37 of the components coupled to said load. The use of several loads in the detector makes it possible to increase the total number of the sensitive elements in the detector without increasing the noise of the readout registrating signals of the amplifiers' integrating capacitor. The ability of the detector filed apart from its increased sensitivity at registration of the radiation also to make the analysis of the space-energy characteristics of the various kinds of radiation studied in the wide range of the intensities makes it possible to substantially expand its operating possibilities and the field of application.

The receptor which has been designed using the detectors described and which can operate with the extra small charges provides a one-step analog-to-digital conversion. The combination of a highly efficient pair of the scintillator and the photodiode alongside with the schematic solution filed increases the sensitivity and precision at registrating the intensities of X-radiation and also expands the dynamic range of the X-radiation intensities being registered.

This in its turn provides the possibility to substantially decrease the dose of X-radiation during examination and to improve the quality of X-ray images. The use of the technical solutions filed makes it possible to conduct safe X-ray examinations not only of people suffering from various diseases (the patients), but also of a large number of healthy people, the passengers for example.

The present invention is not limited by the above-mentioned examples.

What is claimed is:

1. A method of X-ray examination of a body comprising:
    forming a flat fan vertical beam of X-ray radiation of low intensity by passing an X-radiation of low intensity from a radiation source through a collimator connected to said source with a telescopic bar;
    scanning with said fan flat vertical beam of X-radiation due to movement of said collimator and a receptor of X-radiation in a horizontal plane in relation to the body;
    receiving X-radiation transmitted by the body;
    converting X-radiation into visible light radiation which is further converted into electronic signals; and
    shaping and analyzing the electronic signals.

2. A method as in claim 1, wherein the movement of said flat vertical beam of X-radiation is provided by means of moving a collimator in said horizontal plane with a permanent ratio of moving, speeds of said collimator and said receptor of X-radiation.

3. A method as in claim 2, wherein movement of said collimator is provided by means of a step motor.

4. A method as in any of claims from 1 to 3 wherein movement of said receptor of X-radiation is provided by means of a step motor with synchronization of the movement of a collimator and said receptor of X-radiation being effected due to maintaining a pre-defined ratio of rotation frequencies of both step motors.

5. A method as in claim 1, wherein visible light radiation generated from X-radiation received at each scanning moment is directly converted into digital signals.

6. An apparatus for X-ray examination of a body, comprising:
    a carrier for positioning the body;
    an information processing device;
    a source of X-radiation of low intensity and a holder with positioned on said holder a vertical collimator and a receptor of X-radiation;
    said receptor being a vertical array of X-radiation detectors, each of said detectors comprising a first device for converting X-radiation transmitted by the body into visible light radiation and an adjoining second device for converting visible light radiation into an electronic signal;
    said apparatus being supplied by two guides, and said collimator and said receptor of X-radiation being autonomously movable along said guides; and
    the source of X-radiation rotating around a vertical axis of said source, and the source of X-radiation being connected by a telescopic bar to the collimator.

7. An apparatus as in claim 6, wherein said collimator is made in the form of at least one pair of parallel plates.

8. An apparatus as in claim 6, wherein said two guides being first and second guides, said first guides for moving said receptor of X-radiation and said second guides for moving said collimator, and the guides for moving said receptor of X-radiation and the guides for moving se id collimator being positioned on the holder horizontally.

9. An apparatus as in claim 6, wherein the collimator is supplied with a drive mechanism having a step motor with at least one set of vertical metal plates.

10. An apparatus as in claim 6, wherein the receptor of X-radiation is supplied with a drive mechanism having a step motor, where movement of the receptor is synchronized with movement of the collimator by maintaining a pre-defined ratio of rotational speeds of said step motor.

11. An apparatus as in claim 6, wherein the holder is positioned horizontally, said holder moving parallel to itself in relation to a stationary fixed carrier for supporting; the body.

12. An apparatus as in claim 6, wherein the second device of said X-radiation detector is made for converting visible light radiation directly into a digital signal.

13. A method of X-ray examination of a body comprising:
  passing said body through a holder, said holder being defined by a first substantially vertical rack for securing a radiation receptor, a second substantially vertical rack for securing a collimator, and a member connected between said vertical racks, each of said vertical racks and said member having a long axis, each long axis being mutually coplanar;
  pre-shaping a stationary fan-flat vertical beam of X-radiation of low intensity with said collimator;
  receiving X-radiation transmitted by the body;
  converting said X-radiation into visible light radiation which is further converted into electronic signals;
  generating an analysis of the electronic signals; and
  said beam of X-radiation being positioned such that the horizontal plane traversing the bottom of the body cuts off said beam by 2–5 degrees.

14. A method as in claim 13, wherein the beam of X-radiation is shaped at a scattering angle in a vertical plane of 37–43 degrees.

15. A method as in claim 13, wherein visible light radiation generated from X-radiation received at any scanning moment is directly converted into digital signals.

16. An apparatus for X-ray examination of a body, comprising:
  a carrier for positioning the body;
  an information processing device;
  a source of X-radiation of low intensity and a holder with positioned thereon a vertical collimator and a receptor of X-radiation;
  said receptor being a vertical array of X-radiation detectors, each of said detectors comprising a first device for converting X-radiation transmitted by the body into visible light radiation and an adjoining second device for converting visible light radiation into an electronic signal;
  said holder being $\pi$-shaped and being positioned vertically;
  said $\pi$ shaped holder comprising a first substantially vertical rack for securing said radiation receptor, a second substantially vertical rack for securing said collimator and a top member connected between said vertical racks, each of said vertical racks and said top member having a long axis, each long axis being mutually coplanar;
  the carrier for positioning the body being movable in a horizontal plane between the racks of the holder transversely to a plane of said holder, and
  said beam of X-radiation being positioned such that the horizontal plane traversing the bottom part of the body cuts off said beam by 2–5 degrees.

17. An apparatus as in claim 16, wherein the collimator is secured inside said second rack.

18. An apparatus as in claim 16, wherein the source of X-radiation is positioned in an outward part of said second rack.

19. An apparatus as in claim 18, wherein the source of X-radiation is positioned 20–50 percent higher than the level of the carrier.

20. An apparatus as in one of claims 16 and 17 to 19, wherein space between the source of X-radiation and a second rack is covered by an additional housing, made in the form of a pyramid with a base closely adjoining said rack and an angle at the top equal to a largest angle of scattering of said beam.

21. An apparatus as in claim 20, wherein said apparatus is provided with at least one additional collimator made in the form of a pair of parallel plates positioned vertically inside said additional housing.

22. An apparatus as in claim 16, wherein a receptor of X-radiation is comprised of at least two parts with the upper one or said parts making up 60–70 percent of the total height of said receptor of X-radiation and positioned at the angle of 4–6 degrees in relation to a vertical plane.

23. An apparatus as in claim 16, wherein the upper bar between said vertical racks is made in the form of four rods passing through respective holes at corners of the four flat rectangular plates positioned pair-wise at one third of the rod's length adjacent each end of said rods with ends of said rods being used for securing to said vertical racks.

24. An apparatus as in claim 16, wherein the second device of said X-radiation detector is made for converting visible light radiation directly to a digital signal.

* * * * *

UNITED STATES PATENT AND TRADEMARK OFFICE
CERTIFICATE OF CORRECTION

| | | |
|---|---|---|
| PATENT NO. | : 7,016,473 B1 | Page 1 of 1 |
| APPLICATION NO. | : 10/363068 | |
| DATED | : March 21, 2006 | |
| INVENTOR(S) | : Vladimir N. Linev and Anatoly I. Semenikov | |

It is certified that error appears in the above-identified patent and that said Letters Patent is hereby corrected as shown below:

Title Page

In the Title, page 1, and column 1 lines 1 and 2, after "Scanning" delete ", an Apparatus for its" and insert --and Apparati for--

In the Title, page 1, and column 1, line 2, after "Implementation" delete "and a Radiation Detector (3 Version)".

In the Detailed Description of the Invention, column 12, line 19, delete "5.0%" and insert --50%--.

In claim 2, column 20, line 27, after "moving," delete ",".

In claim 8, column 20, line 66, delete "se id" and insert --said--.

In claim 11, column 21, lines 11-12, after "supporting," delete ",".

In claim 13, column 21, line 29, delete "an" and insert --and--.

In claim 16, column 22, line 1, delete "π–shaped" and insert --n–shaped--.

In claim 16, column 22, line 3, delete "π–shaped" and insert --n–shaped--.

In claim 22, column 22, line 37 delete "or" and insert --of--.

Signed and Sealed this

Seventeenth Day of April, 2007

JON W. DUDAS
*Director of the United States Patent and Trademark Office*

(12) EX PARTE REEXAMINATION CERTIFICATE (6742nd)
United States Patent
Linev et al.

(10) Number: US 7,016,473 C1
(45) Certificate Issued: Mar. 31, 2009

(54) METHOD OF BODY X-RAY SCANNING, AN APPARATUS FOR ITS IMPLEMENTATION AND A RADIATION DETECTOR (3 VERSION) THEREOF

(75) Inventors: Vladimir N. Linev, Minsk (BY); Anatoly I. Semenikov, Minsk (BY)

(73) Assignee: Naychno-Proizvodstvennoe Chastnoe Unitarnoe Predpriyatie "ADANI", Minsk (BY)

Reexamination Request:
No. 90/008,884, Dec. 4, 2007

Reexamination Certificate for:
Patent No.: 7,016,473
Issued: Mar. 21, 2006
Appl. No.: 10/363,068
Filed: Feb. 28, 2003

Certificate of Correction issued Apr. 17, 2007.

(22) PCT Filed: Aug. 28, 2000
(86) PCT No.: PCT/BY00/00005

§ 371 (c)(1),
(2), (4) Date: Feb. 28, 2003

(87) PCT Pub. No.: WO02/27306
PCT Pub. Date: Apr. 4, 2002

(51) Int. Cl.
*G21K 1/02* (2006.01)

(52) U.S. Cl. .......................................... 378/146; 378/57
(58) Field of Classification Search ........................ None
See application file for complete search history.

(56) References Cited

FOREIGN PATENT DOCUMENTS

| RU | 2126550 C1 | 2/1999 |
|---|---|---|
| SU | 1679311 A1 | 9/1991 |
| WO | PCT/IB99/00930 | 12/1999 |

*Primary Examiner*—Deandra M Hughes

(57) ABSTRACT

The invention relates to the field of engineering physics in particular to the technique for detecting X-radiation, and it may be used for photometry, dosimetry as well as for measuring of space energy characteristics of optical-and-ionizing radiation fields with the aim of body X-ray scanning, human body in particular, to identify thereon or therein some highly undesirable objects or substances both for medical and security applications i.e. to prevent thefts and acts of terrorism and to provide the security of residential and other buildings that is in airports, banks and other high-risk areas. The X-ray screening of the body is realized by means of scanning it with a pre-shaped collimated bunch of X-radiation of low intensity due to moving the body and a source of X-radiation provided relative to one another, reception of X-radiation transmitted by the body, shaping and analysis of the image in its electronic form. It is the aim of the present invention to design a method and an apparatus which alongside with being safe and efficient make it possible to provide full body scanning with high precision. The aim set forth has been achieved by shaping the bunch of X-radiation as a single flat beam while X-radiation received at each scanning instant and converted into visible light radiation is in its turn converted into digital electronic signals. The radiation detectors filed are featuring a decreased noise level alongside with increased sensitivity and precision for registration of the intensity of X-radiation and also an extended dynamic range of X-radiation intensity values being registered which makes it possible to provide implementation of the method and the apparatus filed in the most adavantageous way.

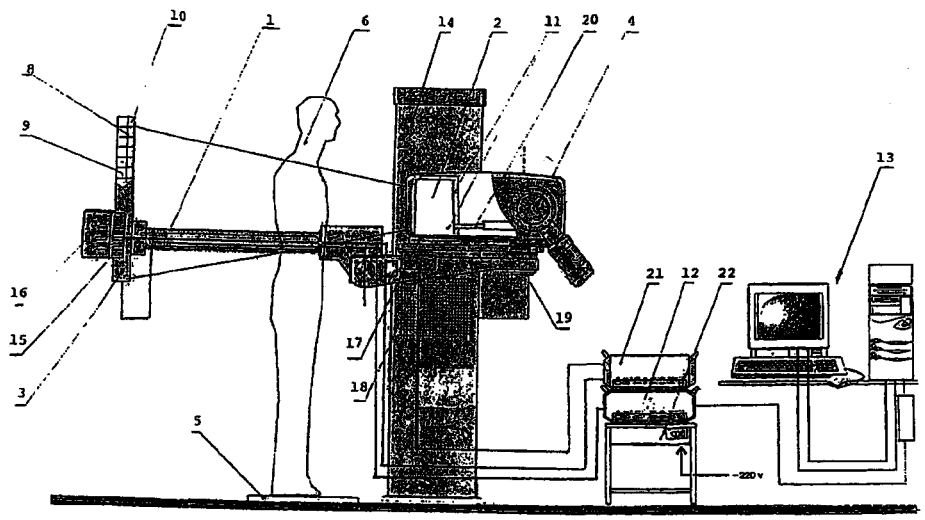

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 13 and 16 are determined to be patentable as amended.

Claims 14–15 and 17–19, dependent on an amended claim, are determined to be patentable.

New claims 25–28 are added and determined to be patentable.

Claims 1–12 and 20–24 were not reexamined.

13. A method of X-ray examination of a body comprising:
passing said body through a holder, said holder being defined by a first substantially vertical rack for securing a radiation receptor, a second substantially vertical rack for securing a collimator, and a member connected between said vertical racks, each of said vertical racks and said member having a long axis, each long axis being mutually coplanar;
pre-shaping a stationary fan-flat vertical beam of X-radiation of low intensity with said collimator;
receiving X-radiation transmitted by the body;
converting said X-radiation into visible light radiation which is further converted into electronic signals;
generating and analysis of the electronic signals; and
[said beam of X-radiation being positioned such that the horizontal plane traversing the bottom of the body cuts off said beam by 2–5 degrees] *wherein an angle between a horizontal plane on which the body is standing, and a bottom boundary of the beam, is a negative 2–5 degrees.*

16. An apparatus for X-ray examination of a body, comprising:
a carrier for positioning the body;
an information processing device;
a source of X-radiation of low intensity and a holder with positioned thereon a vertical collimator and a receptor of X-radiation;
said receptor being a vertical array of X-radiation detectors, each of said detectors comprising a first device for converting X-radiation transmitted by the body into visible light radiation and an adjoining second device for converting visible light radiation into an electronic signal;
said holder being n-shaped and being positioned vertically;
said n-shaped holder comprising a first substantially vertical rack for securing said radiation receptor, a second substantially vertical rack for securing said collimator and a top member connected between said vertical racks, each of said vertical racks and said top member having a long axis, each long axis being mutually coplanar;
the carrier for positioning the body being movable in a horizontal plane between the racks of the holder transversely to a plane of said holder, and
[said beam of X-radiation being positioned such that the horizontal plane traversing the bottom of the body cuts off said beam by 2–5 degrees] *wherein an angle between a horizontal plane on which the body is standing, and a bottom boundary of the beam, is a negative 2–5 degrees.*

25. *A method as in claim 13, wherein the passing step passes the body standing at a full-height through the holder.*

26. *An apparatus as in claim 16, wherein the carrier moves the body standing at a full-height between the racks of the holder.*

27. *An apparatus as in claim 16, wherein the holder is stationary.*

28. *An apparatus as in claim 16, wherein the source of X-radiation is stationary.*

* * * * *